United States Patent [19]
Olsen et al.

[11] Patent Number: 5,994,301
[45] Date of Patent: Nov. 30, 1999

[54] CORPUSCLES OF STANNIUS PROTEIN, STANNIOCALCIN

[75] Inventors: Henrik S. Olsen, Gaithersburg; Mark D. Adams, North Potomac, both of Md.

[73] Assignee: Human Genomes Sciences, Inc., Rockville, Md.

[21] Appl. No.: 08/431,117

[22] Filed: Apr. 28, 1995

Related U.S. Application Data

[63] Continuation-in-part of application No. 08/208,005, Mar. 8, 1994, Pat. No. 5,837,498.

[51] Int. Cl.$^6$ .......................... A61K 38/17; A61K 38/04; C07K 14/435; C07K 14/575
[52] U.S. Cl. ........................... 514/12; 530/399; 530/326; 530/835
[58] Field of Search .................................. 530/350, 399, 530/402, 326, 835; 514/12

[56] References Cited

U.S. PATENT DOCUMENTS

| | | |
|---|---|---|
| 5,447,841 | 9/1995 | Gray et al. . |
| 5,491,224 | 2/1996 | Bittner et al. . |
| 5,538,869 | 7/1996 | Siciliano et al. . |
| 5,545,524 | 8/1996 | Trent et al. . |

FOREIGN PATENT DOCUMENTS

WO/8803949  6/1988  WIPO .

OTHER PUBLICATIONS

Wagner et al. J. Bone Mineral Res 12:165–171, 1997.
Haddad et al. Endocrinol. 137:2113–2117, 1996.
Olsen et al. PNAS 93:1792–1796, 1996.
Lafeber et al. Gen. Comp. Endoccrinol. 69:19–30, 1988.
Wagner et al. Mol. Cell. Endocrinol. 79:129–138, 1991.
Stern et al. J. Bone Mineral Res 6(11):1153–1159, 1991.
Milliken et al. Gen Comp. Endorinol. 77:416–422, 1990.
Wagner, et als., *Molecular and Cellular Endocrinolgy*, vol. 90, No. 1 (1992/1993) pp. 7–15.
Butkus, et als., *Molecular and Cellular Endocrinology*, vol. 54 (1987) pp. 123–133.

*Primary Examiner*—John Ulm
*Assistant Examiner*—Christine Saoud
*Attorney, Agent, or Firm*—A. Anders Brookes

[57] ABSTRACT

The present invention relates to human Corpuscles of Stannius polypeptides and DNA (RNA) encoding such polypeptides. Also provided is a procedure for producing such polypeptides by recombinant techniques and antagonists against such polypeptides. Also provided are methods of using the polypeptide therapeutically for treating renal, bone and heart diseases and for using the antagonists for treating hypocalcemia and osteoporosis. Also provided is a diagnostic assay to detect mutations in the nucleic acid sequence encoding the polypeptide and for altered concentrations of the polypeptide in a sample derived from a host.

16 Claims, 6 Drawing Sheets

```
      GAAACTTCTCAGAGAATGCTCCAAAACTCAGCAGTGCTTCTGGTGCTGGTGATCAGTGCT
      ----------+---------+---------+---------+---------+---------
1                       MetLeuGlnAsnSerAlaValLeuLeuValLeuValIleSerAla  15

TCTGCAACCCATGAGGCGGAGCAGAATGACTCTGTGAGCCCCAGGAAATCCCGAGTGGCG
      +---------+---------+---------+---------+---------+---------
16    SerAlaThrHisGluAlaGluGlnAsnAspSerValSerProArgLysSerArgValAla  35

GCCCAAAACTCAGCTGAAGTGGTTCGTTGCCTCAACAGTGCTCTACAGGTCGGCTGCGGG
      +---------+---------+---------+---------+---------+---------
36    AlaGlnAsnSerAlaGluValValArgCysLeuAsnSerAlaLeuGlnValGlyCysGly  55

GCTTTTGCATGCCTGGAAAACTCCACCTGTGACACAGATGGGATGTATGACATCTGTAAA
      +---------+---------+---------+---------+---------+---------
56    AlaPheAlaCysLeuGluAsnSerThrCysAspThrAspGlyMetTyrAspIleCysLys  75

TCCTTCTTGTACAGCGCTGCTAAATTTGACACTCAGGGAAAAGCATTCGTCAAAGAGAGC
      +---------+---------+---------+---------+---------+---------
76    SerPheLeuTyrSerAlaAlaLysPheAspThrGlnGlyLysAlaPheValLysGluSer  95

TTAAAATGCATCGCCAACGGGGTCACCTCCAAGGTCTTCCTCGCCATTCGGAGGTGCTCC
      +---------+---------+---------+---------+---------+---------
96    LeuLysCysIleAlaAsnGlyValThrSerLysValPheLeuAlaIleArgArgCysSer  115

ACTTTCCAAAGGATGATTGCTGAGGTGCAGGAAGAGTGCTACAGCAAGCTGAATGTGTGC
      +---------+---------+---------+---------+---------+---------
116   ThrPheGlnArgMetIleAlaGluValGlnGluGluCysTyrSerLysLeuAsnValCys  135

AGCATCGCCAAGCGGAACCCTGAAGCCATCACTGAGGTCGTCCAGCTGCCCAATCACTTC
      +---------+---------+---------+---------+---------+---------
136   SerIleAlaLysArgAsnProGluAlaIleThrGluValValGlnLeuProAsnHisPhe  155

TCCAACAGATACTATAACAGACTTGTCCGAAGCCTGCTGGAATGTGATGAAGACACAGTC
      +---------+---------+---------+---------+---------+---------
156   SerAsnArgTyrTyrAsnArgLeuValArgSerLeuLeuGluCysAspGluAspThrVal  175

AGCACAATCAGAGACAGCCTGATGGAGAAAATTGGGCCTAACATGGCCAGCCTCTTCCAC
      ----------+---------+---------+---------+---------+---------
176   SerThrIleArgAspSerLeuMetGluLysIleGlyProAsnMetAlaSerLeuPheHis  195

ATCCTGCAGACAGACCACTGTGCCCAAACACACCCACGAGCTGACTTCAACAGGAGACGC
      +---------+---------+---------+---------+---------+---------
196   IleLeuGlnThrAspHisCysAlaGlnThrHisProArgAlaAspPheAsnArgArgArg  215
```

FIG.1A

```
    ACCAATGAGCCGCAGAAGCTGAAAGTCCTCCTCAGGAACCTCCGAGGTGAGGAGGACTCT
    +---------+---------+---------+---------+---------+---------
216 ThrAsnGluProGlnLysLeuLysValLeuLeuArgAsnLeuArgGlyGluGluAspSer 235

CCCTCCCACATCAAACGCACATCCCATGAGAGTGCATAACCAGGGAGAGGT
    +---------+---------+---------+---------+---------+
236 ProSerHisIleLysArgThrSerHisGluSerAla                         247
```

FIG. 1B

MLQNSAVLLVSVISASATHEAEQNDSVSPRKSRVAAQNSAEVVRCLNSALQVGCGAFACL
ML    + V ++  +A       +  SPR++R ++ + ++V RCLN AL VGCG FACL
MLAKFGLCAVFLVLGTAATFDTDPEEASPRRARFSSNSPSDVAPCLNGALAVGCGTFACL

ENSTCDTDGMYDICKSFLYSAAKFDTQGKAFVKESLKCIANGVTSKVFLAIRRCSTFQRM
ENSTCDTDGM+DIC+ F ++AA F+TQGK FVKESL+CIANGVTSKVF   IRRC  FQRM
ENSTCDTDGMHDICQLFFHTAATFNTQGKTFVKESLRCIANGVTSKVFQTIGGCGVFQRM

IAEVQEECYSKLNVCSIAKRNPEAITEVVQLPNHFSNRYYNRLVRSLLECDEDTVSTIRD
I+EVQEECYS+L++C +A+ NPEAI EVVQ+P HF NRYY+ L++SLL CDE+TV+ +R
ISEVQEECYSRLDICGVARSNPEAIGEVVQVPAHFPNRYYSTLLQSLLACDEETVAVVRA

SLMEKIGPNMASLFHILQTDHCAQ
 L+ ++GP+M +LF +LQ  HC Q
GLVARLGPDMETLFQLLQNKHCPQ 204

FIG.2

CORPUSCLES OF STANNIUS PROTEIN, STANNIOCALCIN

This application is a continuation-in-part of a previous application filed in the United States Patent and Trademark Office on Mar. 8, 1994 and assigned Ser. No. 08/208,005, now U.S. Pat. No. 5,837,498.

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a human Corpuscles of Stannius protein. The invention also relates to inhibiting the action of such polypeptide.

Stanniocalcin (formerly known as both teleocalcin and hypocalcin) is an anti-hypercalcemic, glycoprotein hormone that is produced by the Corpuscles of Stannius, endocrine glands which are confined to bony fishes. The polypeptide of the present invention has a high degree of homology at the amino acid level to the glycoprotein hormone from fish which is involved in the regulation of calcium levels.

The Corpuscles of Stannius protein of non-humans has been studied extensively. Recently, a Corpuscles of Stannius protein has been purified and cloned from *Anquilla australis*. The kidneys of teleost fish have been found to contain secretory granules, the Corpuscles of Stannius. Electron microscopy indicates that the granules are of a proteinaceous nature and may represent hormones or enzymes of unrecognized physiological and biochemical function (Butkus, A. et al. Mol. Cell Endocrinol, 54:123–33 (1987)).

There has also been isolated and purified a glycoprotein from the Corpuscles of Stannius of trout, which is considered hypocalcin, the major hypocalcemic hormone of fish. This product is present in relatively large amounts in the Corpuscles of Stannius of several species (i.e., European eel, tilapia goldfish, and carp). Hypocalcin is typically released from the Corpuscles of Stannius in response to an experimentally induced increase of the blood calcium concentration. Ultrastructural observations show that after this treatment the hypocalcin-producing cell type of the corpuscles of stannius are almost completely degranulated. The isolated glycoprotein has an apparent molecular weight of 54 Kda (Lafeber F. P. et al., Gen Comp. Endocrinol, 69:19–30 (1988)).

Moreover, it has recently been shown that several synthetic peptide fragments of teleocalcin inhibit calcium uptake in juvenile rainbow trout (*Salmo Gairdneri*). The N-terminal peptides (amino acids 1 to 20) of both eel and salmon teleocalcin significantly inhibit $Ca^{45}$ uptake at the high point of the calcium uptake cycle (up to 75%), although the effective doses of the peptides on a molar basis were 20 to 200 times that of the intact molecule. In contrast, the C-terminal fragment of eel teleocalcin (amino acids 202 to 231) did not have an inhibitory effect on calcium uptake (Milliken C. E. et al., Gen. Comp. Endocrinol, 77:416–22 (1990)).

There has also been a description of the purification and characterization of two salmon stanniocalcins, and the examination of the regulation of hormone secretion in response to calcium using both an in vitro and in vivo model systems. The molecular cloning and cDNA sequence analysis of a coho salmon stanniocalcin messenger RNA (mRNA) from a salmon CS lambda gt10 cDNA library is described. The stanniocalcin mRNA in salmon is approximately 2 Kda in length and encodes a primary translation product of 256 amino acids. The first 33 residues comprise the preprotein region of the hormone, whereas the remaining 223 residues make up the mature form of the hormone (Wagner G. F. et al., Mol. Cell Endocrinol, 90:7–15 (1992)).

In accordance with one aspect of the present invention, there are provided novel mature polypeptides of the present invention, as well as biologically active and diagnostically or therapeutically useful fragments, analogs and derivatives thereof. The proteins of the present invention are of human origin.

In accordance with another aspect of the present invention, there are provided isolated nucleic acid molecules encoding such polypeptide, including mRNAs, DNAs, cDNAs, genomic DNA as well as biologically active and diagnostically or therapeutically useful fragments, analogs and derivatives thereof.

In accordance with another aspect of the present invention there are provided nucleic acid probes comprising nucleic acid molecules of sufficient length to specifically hybridize to nucleic acid sequences encoding the polypeptides of the present invention.

In accordance with a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided processes for utilizing such polypeptides, or polynucleotides encoding such polypeptides for therapeutic purposes, for example, treatment of electrolyte disorders which lead to renal, bone and heart diseases, and disorders due to elevated bone resorption, e.g. osteoporosis and Paget's disease.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of hypocalcemia resulting in tetany, convulsions and other related disorders, and osteoporosis.

In accordance with another aspect of the present invention there is provided a method of diagnosing a disease or a susceptibility to a disease related to a mutation in the nucleic acid sequences and the polypeptides encoded thereby of the invention.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1B (collectively FIG. 1) displays the cDNA sequence and corresponding deduced amino acid sequence of the preprocessed Corpuscles of Stannius protein. The amino acid sequence is shown below using the standard 3 letter abbreviation code.

FIG. 2 displays the comparison of the polypeptide of the present invention (upper line, see SEQ ID NO:2) to the stanniocalcin isolated from *Oncorhynchus kisutch* (lower line, see SEQ ID NO:10). The middle line polypeptide FIG. 2 (SEQ ID NO:9) shows the amino acids which the polypeptide according to the invention and the polypeptide of SEQ ID NO:10 have in common. Such common amino acid residues are not a contiguous sequence, but for ease of listing are provided in SEQ ID NO:9 as contiguous sequence. No apparent sequence homology exists beyond amino acid 204 of the stanniocalcin from *Oncorhynchus kisutch*. Total length of stanniocalcin isolated from *Oncorhynchus kisutch* is 256 amino acids.

Figure 3:
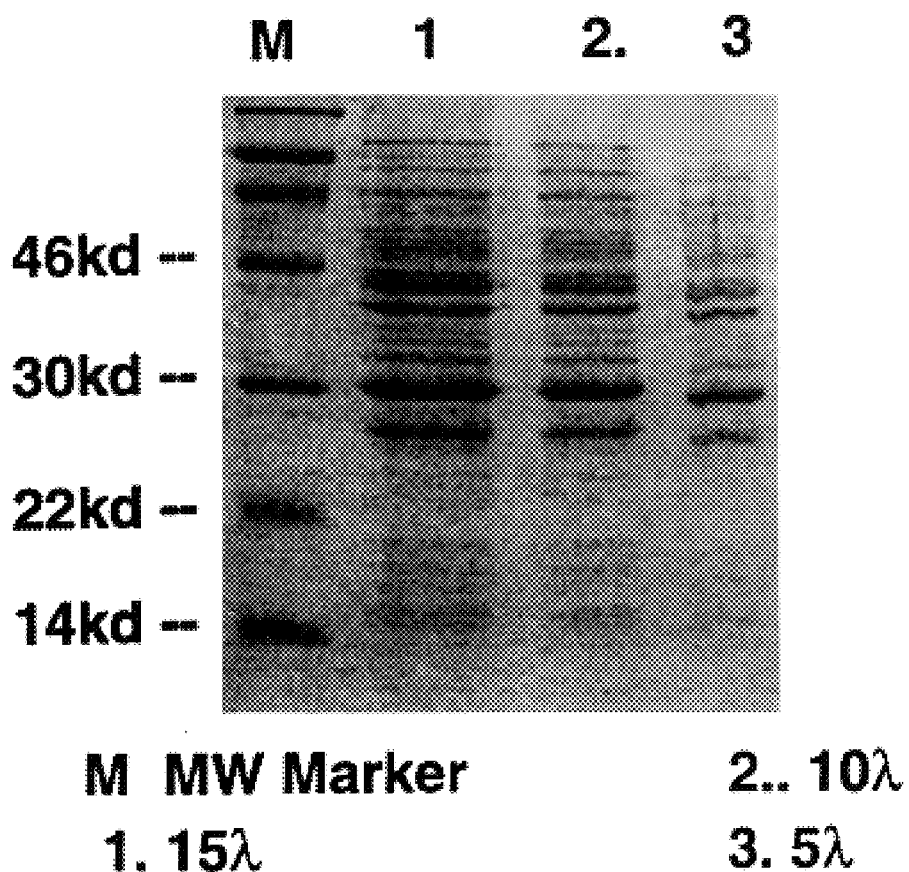
FIG. 3 shows the banding pattern of the human stanniocalcin polypeptide following bacterial expression and purification.

In accordance with one aspect of the present invention, there are provided isolated nucleic acids which encode for the mature polypeptide having the deduced amino acid sequence of FIG. 1 (SEQ ID No. 2), or for the mature polypeptide encoded by the cDNA of the clone deposited as ATCC Deposit No. 75652 on Jan. 25, 1994.

The ATCC number referred to above is directed to a biological deposit with the ATCC, 12301 Parklawn Drive, Rocville, Md. 20852. Since the strain referred to is being maintained under the terms of the Budapest Treaty, it will be made available to a patent office signatory to the Budapest Treaty.

The polynucleotide of the present invention was isolated from a human early stage lung cDNA library. It contains an open reading frame encoding a prepropolypeptide of 247 amino acids, wherein the first 33 amino acids represent a putative leader sequence such that the mature active polypeptide comprises 214 amino acids. The polypeptide exhibits a high degree of homology to Stanniocalcin from *Anguilla australis*, with 119 identical amino acids (61%) in a 195 amino acid overlap. It also has a very high homology to stanniocalcin from *Oncorhynchus kisutch*, with 118 identical amino acids (57%) in a 204 amino acid overlap.

The polynucleotide of the present invention may be in the form of RNA or in the form of DNA, which DNA includes cDNA, genomic DNA, and synthetic DNA. The DNA may be double-stranded or single-stranded and if single stranded may be the coding strand or non-coding (anti-sense) strand. The coding sequence which encodes the mature polypeptide may be identical to the coding sequence shown in FIG. 1 (SEQ ID No. 1) or that of the deposited clone or may be a different coding sequence, which coding sequence, as a result of the redundancy or degeneracy of the genetic code, encodes the same, mature polypeptide as the DNA of FIG. 1 or the deposited cDNA.

The polynucleotide which encodes for the mature polypeptide of FIG. 1 (SEQ ID No. 2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID No. 2) or the same mature polypeptide encoded by the cDNA of the deposited clone as well as variants of such polynucleotides which variants encode for a fragment, derivative or analog of the polypeptide of FIG. 1 (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID No. 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. Preferably, the marker sequence is a hexa-histidine tag supplied by a pQE-9 vector (Qiagen, Inc., Chatsworth, Calif.) to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 (SEQ ID No. 1) or the deposited cDNA.

Alternatively, the polynucleotide may be a polynucleotide which has at least 20 bases, preferably 30 bases, and more preferably at least 50 bases which hybridize to a polynucleotide of the present invention and which has an identity thereto, as hereinabove described, and which does not retain activity. Such polynucleotides may be employed as probes for the polynucleotide of SEQ ID No. 1, for example, for recovery of the polynucleotide or as a diagnostic probe or as a PCR primer.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. β 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to a Corpuscles of Stannius polypeptide which has the deduced amino acid sequence of FIG. 1 (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide, for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the Human Corpuscles of Stannius genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda P promoter and other promoters known to control expression of genes in prokaryotic or eukaryotic cells or their L
viruses.

The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as *Drosophila S2* and *Spodoptera Sf9*; animal cells such as HEK, CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBs, pD10, phagescript, PsiX174, Pbluescript SK, Pbsks, pNH8a, pNH16a, pNH18a, pNH46a (Stratagene); pTRC99A, pKK223-3, pKK233-3, pDR540, pRIT5 (Pharmacia). Eukaryotic: PWLNEO, pSV2cat, pOG44, pXT1, PSG (Stratagene) pSVK3, PBPV, PMSG, PSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P , P and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, (Cold Spring Harbor, N.Y., 1989), the disclosure of which is hereby incorporated by reference.

Transcription of the DNA encoding the polypeptide of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), ¬-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Corpuscles of Stannius protein is recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

The polypeptide of the present invention may be employed for therapeutic treatment of numerous electrolyte-based diseases. One cause of arterial hypertension is abnormal $Na^+$ transport across the cell wall of the vascular smooth cells due to a defect in or inhibition of the Na—K pump, another is increased permeability to $Na^+$ as has been described in some forms of human hypertension. The net result is increases in intracellular $Na^+$, which makes the cell more sensitive to vasoconstrictive agents. Since $Ca^{++}$ follows $Na^+$, it is postulated that it is the accumulation of intracellular $Ca^{++}$ and not $Na^+$ per se that is responsible for increased sensitivity to sympathetic stimulation.

Figure 4:
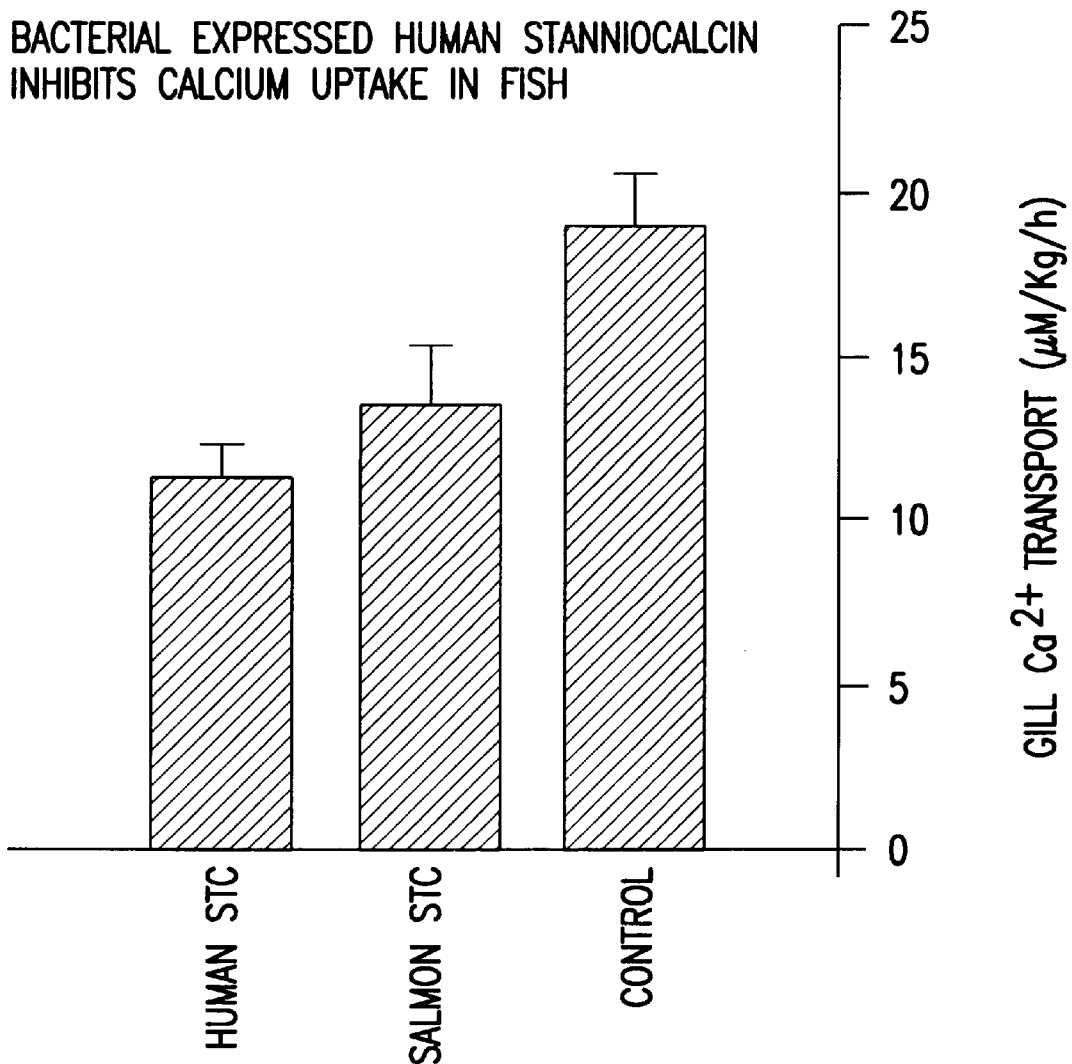
FIG. 4 illustrates that the polypeptide of the present invention (Human SCT) inhibits calcium transport in fish as compared to salmon stanniocalcin (salmon SCT) and a control wherein no stanniocalcin was injected.

The results of Example 4, as shown in FIG. 4, suggest that human Corpuscles of Stannius protein is an effective inhibitor of calcium uptake when compared to the amount of calcium uptake in its absence (control).

Accordingly, since Corpuscles of Stannius protein can function as a hypocalcemic agent it can help to offset this increased intracellular $Ca^{++}$ and reduce or prevent hypertension. Further, hypercalcemia has been implicated in heart dysrhythmias, coma and cardiac arrest. Accordingly, the Corpuscles of Stannius protein may have therapeutic value for the treatment of these disorders by lowering the concentration of free calcium.

Hypertension is also directly related to renal disorders. Accordingly, a higher or lower than normal concentration of electrolytes can cause renal malfunction and directly lead to other more serious disorders. As an example calcium-phosphorus imbalance can cause muscle and bone pain, demineralization of the bones and calcification in various organs including the brain, eyes, myocardium and blood vessels.

Figure 5:
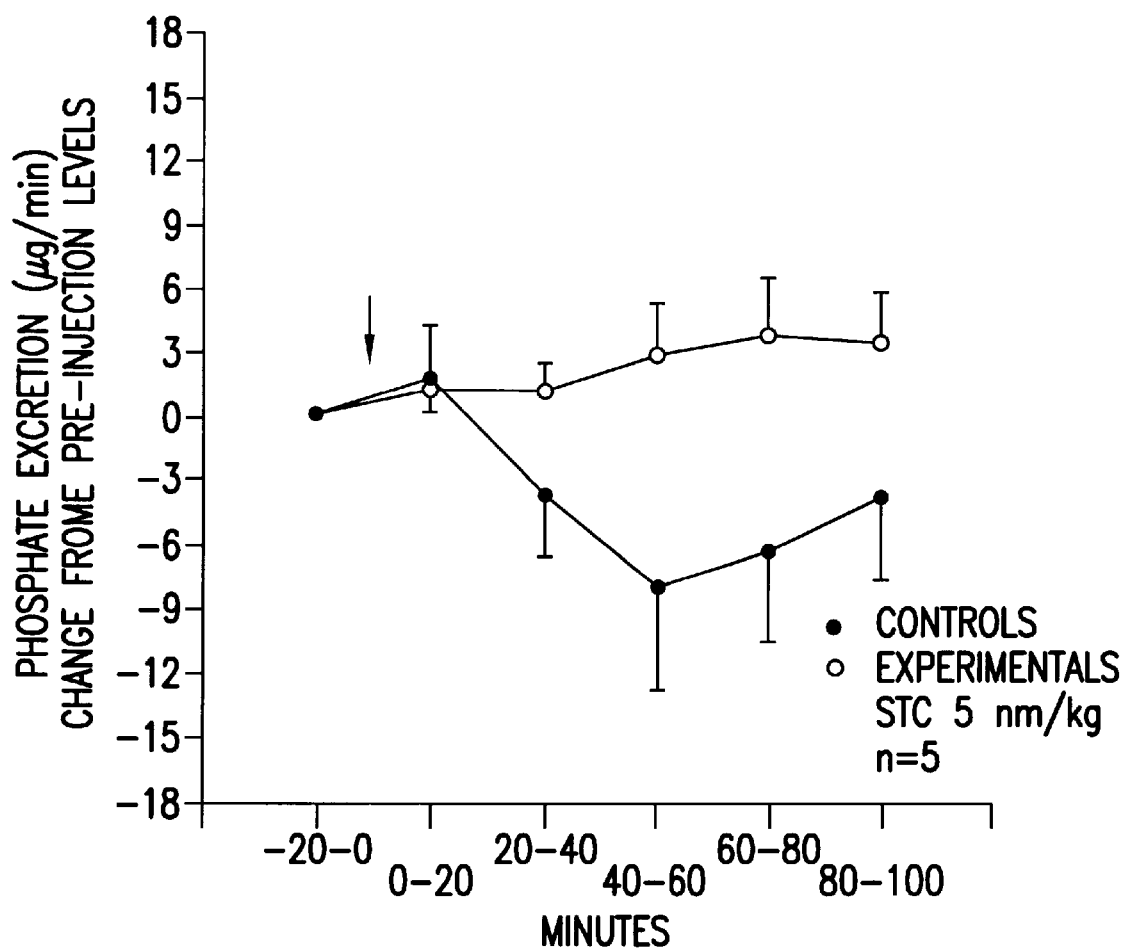
FIG. 5 is an illustration of the results of injecting rats with a polypeptide of the present invention which shows that renal excretion of phosphate was significantly reduced compared to the control animals.

As shown in Example 5, the results of which are depicted in FIG. 5, the Corpuscles of Stannius protein of the present invention regulates renal excretion of phosphate. Accordingly, the polypeptide of the present invention may be employed to offset disorders that are due to a calcium-phosphate imbalance. Renal failure itself leads to an abnormally high concentration of phosphate in the blood which can be reduced to normal concentrations by the polypeptide of the present invention.

Similarly, the polypeptide of the present invention may also be employed for the treatment of certain bone diseases. For example, excessive concentrations of calcium lead to the development of fibrous nodules in affected bone.

The causes of hypercalcemia may also be a number of different disorders including hyperparathyroidism, hypervitaminosis D, tumors that raise the serum calcium levels by destroying bone, sarcoidosis, hyperthyroidism, adrenal insufficiency, loss of serum albumin secondary to renal diseases, excessive GI calcium absorption and elevated concentration of plasma proteins. Accordingly, Corpuscles of Stannius protein is effective in reducing hypercalcemia and its related disorders.

Corpuscles of Stannius protein may also be employed for the treatment of other disorders relating to unusual electrolyte concentrations and fluid imbalance, for example, migraine headaches.

The polynucleotides and polypeptides encoded by such polynucleotides may also be utilized for in vitro purposes related to scientific research, synthesis of DNA and manufacture of DNA vectors and for designing therapeutics and diagnostics for the treatment of human disease.

Fragments of the full length Corpuscles of Stannius gene may be used as a hybridization probe for a cDNA library to isolate the full length gene and to isolate other genes which have a high sequence similarity to the Corpuscles of Stannius gene or similar biological activity. Probes of this type generally have at least 20 bases. Preferably, however, the probes have at least 30 bases and may contain, for example, 50 or more bases. In many cases, the probe has from 20 to 50 bases. The probe may also be used to identify a cDNA clone corresponding to a full length transcript and a genomic clone or clones that contain the complete Corpuscles of Stannius gene including regulatory and promotor regions, exons, and introns. An example of a screen comprises isolating the coding region of the Corpuscles of Stannius gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention is also related to the use of the Corpuscles of Stannius gene as part of a diagnostic assay for detecting diseases or susceptibility to diseases related to the presence of mutations in the Corpuscles of Stannius nucleic acid sequences. Such diseases are related to under-expression of the Corpuscles of Stannius polypeptides, for example, elevated calcium concentration.

Individuals carrying mutations in the Corpuscles of Stannius gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding Corpuscles of Stannius protein can be used to identify and analyze Corpuscles of Stannius gene mutations. For example, deletions and insertions can be detected by a change in size of the amplified product in comparison to the normal genotype. Point mutations can be identified by hybridizing amplified DNA to radiolabeled Corpuscles of Stannius RNA or alternatively, radiolabeled Corpuscles of Stannius antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of Corpuscles of Stannius protein in various tissues since an over-expression of the proteins compared to normal control tissue samples may detect the presence of a disease or susceptibility to a disease. Assays used to detect levels of Corpuscles of Stannius protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the Corpuscles of Stannius antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein, for example, bovine serum albumen (BSA). Next, the monoclonal antibody is incubated in the dish during which time the monoclonal antibodies attach to any Corpuscles of Stannius proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to Corpuscles of Stannius. Unattached reporter antibody is then washed out. Peroxidase substrates are then added to the dish and the amount of color developed in a given time period is a measurement of the amount of Corpuscles of Stannius protein present in a given volume of patient sample when compared against a standard curve.

A competition assay may be employed wherein antibodies specific to Corpuscles of Stannius protein are attached to a solid support and labeled Corpuscles of Stannius protein and a sample derived from the host are passed over the solid support and the amount of label detected, for example by liquid scintillation chromatography, can be correlated to a quantity of Corpuscles of Stannius protein in the sample.

A "sandwich" assay is similar to an ELISA assay. In a "sandwich" assay Corpuscles of Stannius is passed over a solid support and binds to antibody attached to a solid support. A second antibody is then bound to the Corpuscles of Stannius protein. A third antibody which is labeled and specific to the second antibody is then passed over the solid support and binds to the second antibody and an amount can then be quantified.

This invention provides a method for identification of the receptors for the Corpuscles of Stannius polypeptides. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention provides a method of screening compounds to identify agonists and antagonists to the human Corpuscles of Stannius polypeptides of the present invention. An agonist is a compound which has similar biological functions of the polypeptides, while antagonists block such functions. An example of such a bioassay comprises injecting human Corpuscles of Stannius protein into a species of fish and exposing the fish to labeled calcium in the presence of the compound to be screened. A comparative control assay is also performed. The ability of the compound to inhibit uptake of calcium, or increase the uptake, can then be quantified such as by liquid scintillation spectrophotometry.

Alternatively, a mammalian cell or membrane preparation expressing the receptors of the polypeptide would be incubated with a labeled human Corpuscles of Stannius polypeptide, eg. by radioactivity, in the presence of the compound. The ability of the compound to block or enhance this interaction could then be measured.

Examples of potential Corpuscles of Stannius antagonists include antibodies, or in some cases, oligonucleotides, which bind to the polypeptides. Another example of a potential antagonist is a negative dominant mutant of the polypeptide. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (Triple- helix, see Lee et al., Nucl. Acids Res., 6:3073 (1979); Cooney et al, Science, 241:456 (1988); and Dervan et al., Science, 251: 1360 (1991)), thereby preventing transcription and the production of the human Corpuscles of Stannius polypeptide. The antisense RNA oligonucleotide hybridizes to the mRNA in vivo and blocks translation of the mRNA molecule into the polypeptides (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the human Corpuscles of Stannius polypeptides.

Another potential human Corpuscles of Stannius antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to inhibit the hypocalcemic effects of the human Corpuscles of Stannius protein, and to treat osteoporosis and Paget's Diseases, among other disorders where an increase of calcium levels is desired.

The antagonists may be employed in a composition with a pharmaceutically acceptable carrier, e.g., as hereinafter described.

The human Corpuscles of Stannius protein and agonists and antagonists may be employed in combination with a suitable pharmaceutical carrier. Such compositions comprise a therapeutically effective amount of the polypeptide, antagonist or agonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, agonists or antagonists may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the polypeptides will be administered in an amount of at least about 10 g/kg body weight and in most cases they will be administered in an amount not in excess of about 8 mg/Kg body weight per day. In most cases, the dosage is from about 10 g/kg to about 1 mg/kg body weight daily, taking into account the routes of administration, symptoms, etc.

The human Corpuscles of Stannius protein, and agonists or antagonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding the polypeptide ex vivo, with the engineered cells then being provided to a patient to be treated with the polypeptide. Such methods are well-known in the art. For example, cells may be engineered by procedures known in the art by use of a retroviral particle containing RNA encoding the polypeptide of the present invention.

Similarly, cells may be engineered in vivo for expression of the polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The retroviral plasmid vectors may be derived from retroviruses which include, but are not limited to, Moloney Murine Sarcoma Virus, Moloney Murine Leukemia Virus, spleen necrosis virus, Rous Sarcoma Virus and Harvey Sarcoma Virus.

In a preferred embodiment the retroviral expression vector, pMV-7, is flanked by the long terminal repeats (LTRs) of the Moloney murine sarcoma virus and contains the selectable drug resistance gene neo under the regulation of the herpes simplex virus (HSV) thymidine kinase (tk) promoter. Univque EcoRI and HimdIII sites facilitate the introduction of coding sequence (Kirschmeier, P. T. et al., DNA, 7:219–25 (1988)).

The vectors include one or more suitable promoters which include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and -actin promoters). The selection of a suitable promoter will be apparent to thsoe skilled in the art from the teachings contained herein.

The nucleic acid sequence encoding the polypeptide of the present invention is under the control of a suitable promoter which includes, but is not limited to, viral thymidine kinase promoters, such as the Herpes Simplex thymidine kinase promoter; retroviral LTRs, the -actin promoter, and the native promoter which controls the gene encoding the polypeptide.

The retroviral plasmid vector is employed to transduce packaging cell lines to form producer cell lines. Examples of packaging cells which may be transfected include, but are not limited to, the PE501, PA317 and GP+am12. The vector may transduce the packaging cells through any means known in the art. Such means include, but are not limited to, electroporation, the use of liposomes, and CaPO precipitation.

The producer cell line generates infectious $$\text{retroviral}^4$$

vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced, include but are not limited to, fibroblasts and endothelial cells.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than that have a higher likelihood of binding to a unique chromosomal location with sufficient signal intensity for simple detection. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Corpuscles of Stannius Protein

The DNA sequence encoding Corpuscles of Stannius Protein, ATCC # 75652, is initially amplified using PCR oligonucleotide primers corresponding to the 5' and 3' end sequences of Corpuscles of Stannius nucleic acid sequence. Additional nucleotides corresponding to the SphI and BglII restriction enzyme site were added to the 5' and 3' sequences respectively. The 5' oligonucleotide primer has the sequence 5' GACTGCATGCTCCAAAACTCAGCAGTG 3' (SEQ ID No. 3), contains a SphI restriction enzyme site and 21 nucleotides of Corpuscles of Stannius Protein coding sequence starting from the initiation codon; the 3' sequence 3' GACTAGATCTTGCACTCTCATGGGATGTGCG 5' (SEQ ID No. 4) contains complementary sequences to a BglII restriction site (AGATCT) and the last 21 nucleotides of Corpuscles of Stannius Protein coding sequence. The restriction enzyme sites correspond to the restriction enzyme sites on the bacterial expression vector pQE70 (Qiagen, Inc. Chatsworth, Calif.). pQE70 encodes antibiotic resistance (Amp$^r$), a bacterial origin of replication (ori), an IPTG-regulatable promoter operator (P/O), a ribosome binding site (RBS), a 6-His tag and restriction enzyme sites. pQE70 was then digested with the SphI and BglII restriction enzymes. The amplified sequences were ligated into pQE70 and were inserted in frame with the sequence encoding for the histidine tag and the RBS. The ligation mixture was then used to transform E. coli strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG (Isopropyl-B-D-thiogalacto pyranoside) was then added to a final concentration of 1 mM. IPTG induces by inactivating the lacI repressor, clearing the P/O leading to increased gene expression. Cells were grown an extra 3 to 4 hours. Cells were then harvested by centrifugation (20 mins at 6000×g). The cell pellet was solubilized in the chaotropic agent 6 Molar Guanidine HCl. After clarification, solubilized stanniocalcin was purified from this solution by chromatography on a Nickel-Chelate column under conditions that allow for tight binding by proteins containing the 6-His tag (Hochuli, E. et al., Genetic Engineering, Principles & Methods, 12:87–98 (1990). Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate. The purified protein was analyzed by SDS-PAGE (FIG. 3).

EXAMPLE 2

Cloning and Expression of Human Stanniocalcin Using the Baculovirus Expression System The DNA sequence encoding the full length human Stanniocalcin protein, ATCC # 75652, was amplified using PCR oligonucleotide primers corresponding to the 5' and 3' sequences of the gene:

The 5' primer has the sequence 5' CAGTGGATCCGC-CACC<u>ATG</u>CTCCAAAACTCAGCAGTG 3' (SEQ ID No. 5) and contains a BamHI restriction enzyme site (in bold) followed by 6 nucleotides resembling an efficient signal for the initiation of translation in eukaryotic cells (Kozak, M., J. Mol. Biol., 196:947–950 (1987) which is just behind the first 21 nucleotides of the human Corpuscles of Stannius gene (the initiation codon for translation "ATG" is underlined).

The 3' primer has the sequence 5' CAGTGGTACCGGT-TGTGAATAACCTCTCCC 3' (SEQ ID No. 6) and contains the cleavage site for the restriction endonuclease Asp718 and 20 nucleotides complementary to the 3' non-translated sequence of the Corpuscles of Stannius gene. The fragment was digested with the endonucleases BamHI and Asp718 and then purified again on a 1% agarose gel. This fragment is designated F2.

The vector pRG1 (modification of pVL941 vector, discussed below) is used for the expression of the human Corpuscles of Stannius protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp718. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and Asp718 and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E. coli* HB101 cells were then transformed and bacteria identified that contained the plasmid (pBac-hSTC) with the human Corpuscles of Stannius gene using the enzymes BamHI and Asp718. The sequence of the cloned fragment was confirmed by DNA sequencing.

5 μg of the plasmid pBac-hSTC was co-transfected with 1.0 μg of a commercially available linearized baculovirus ("BaculoGold baculovirus DNA", Pharmingen, San Diego, Calif.) using the lipofection method (Felgner et al. Proc. Natl. Acad. Sci. USA, 84:7413–7417 (1987)).

1 μg of BaculoGold virus DNA and 5 μg of the plasmid pBac-hSTC were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 278° C. After 5 hours the transfection solution was removed from the plate and 1 ml of Grace's insect medium supplemented with 10% fetal calf serum was added. The plate was put back into an incubator and cultivation continued at 278° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 48° C.

Sf9 cells were grown in Grace's medium supplemented with 10% heat-inactivated FBS. The cells were infected with the recombinant baculovirus V-hSTC at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 3

Cloning and Expression of Human Corpuscles of Stannius Protein Using Chinese Hamster Ovary Cells Lacking Dihydrofolate Activity The vector pN346 is used for the expression of the human Corpuscles of Stannius protein. Plasmid pN346 is a derivative of the plasmid pSV2-DHFR [ATCC Accession No. 37146]. Both plasmids contain the mouse dihydrolfolate reductase (DHFR) gene under control of the SV40 early promoter. Chinese hamster ovary, or other cells, lacking dihydrofolate activity that are transfected with these plasmids can be selected by growing the cells in a selective medium (alpha minus MEM, Life Technologies) supplemented with the chemotherapeutic agent methotrexate (MTX). The amplification of the DHFR genes in cells resistant to methotrexate has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and overexpressed. It is state of the art to develop cell lines carrying more than 1000 copies of the genes. Subsequently, when the methotrexate is withdrawn, cell lines contain the amplified gene integrated into the chromosome(s).

Plasmid pN346 contains a strong promoter for the expression of the gene of interest, namely, the long terminal repeat (LTR) of the Rous Sarcoma Virus (Cullen et al., Molecular and Cellular Biology, March 1985, 438–447) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes; BamHI, PvuII, and NruI. Behind these cloning sites, the plasmid contains translational stop codons in all three reading frames followed by the 3' intron and the polyadenylation site of the rat preproinsulin gene. Other high efficient promoters can also be used for expression, e.g., the human -actin promoter, the SV40 early or late promoters or the long terminal repeats from other retroviruses, e.g., HIV and HTLVI. For the polyadenylation of mRNA, other signals, e.g., from the human growth hormone or globin genes, may be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g., G418 plus methotrexate.

The plasmid pN346 was digested with the restriction enzyme BamHI and then dephosphorylated using calf intestinal phosphatase by procedures known in the art. The vector was then isolated from a 1% agarose gel.

The DNA sequence encoding human Corpuscles of Stannius protein, ATCC # 75652, was amplified using PCR oligonucleotide primers corresponding to the 5' and 3' sequences of the gene:

The 5' primer has the sequence 5' CAGTGGATCCGC-CACCATGCTCCAAAACTCAGCAGTG 3' (SEQ ID No. 7) and contains a BamHI restriction enzyme site (in bold) followed by 6 nucleotides resembling the efficient signal for translation (Kozak, M., supra) plus the first 21 nucleotides of the gene (the initiation codon for translation "ATG" is underlined).

The 3' primer has the sequence 5' CAGTGGATCCGGT-TGTGAATAACCTCTCCC 3' (SEQ ID No. 8) and contains the cleavage site for the restriction endonuclease BamHI and 20 nucleotides complementary to the 3' non-translated sequence of the gene.

The amplified fragments digested with the endonuclease BamHI and then purified on a 1% agarose gel.

The isolated fragment and the dephosphorylated vector were then ligated with T4 DNA ligase. *E. coli* HB101 cells were then transformed and bacteria identified that contained the plasmid pN346hSTC inserted in the correct orientation. The sequence of the inserted gene was confirmed by DNA sequencing.

Transfection of CHO-DHFR-Cells

Chinese hamster ovary cells lacking an active DHFR enzyme were used for transfection. 5 µg of the expression plasmid pN346hSTC were co-transfected with 0.5 µg of the plasmid pSVneo using the lipofection method (Felgner et al., supra). The plasmid pSV2-neo contains a dominant selectable marker, the gene neo from Tn5 encoding an enzyme that confers resistance to a group of antibiotics including G418. The cells were seeded in alpha minus MEM supplemented with 1 mg/ml G418. After 2 days, the cells were trypsinized and seeded in hybridoma cloning plates (Greiner, Germany) and cultivated for 10–14 days. After this period, single clones were trypsinized and then seeded in 6-well petri dishes using different concentrations of methotrexate (25, 50 nm, 100 nm, 200 nm, 400 nm). Clones growing at the highest concentrations of methotrexate were then transferred to new 6-well plates containing even higher concentrations of methotrexate (500 nM, 1 µM, 2 µM, 5 µM). The same procedure was repeated until clones grew at a concentration of 100 µM.

The expression of the desired gene product was analyzed by Western blot analysis and SDS-PAGE.

EXAMPLE 4
Human Corpuscles of Stannius Protein Inhibits Calcium Uptake in Fish Goldfish (1.2–0.1 g; 10 fish per group were given intraperitoneal injections of bacterial expressed human STC (10 mg/kg), salmon STC (1 mg/kg) or saline and placed in tanks of $^{45}$Ca water (50.000 dpm/ml) for 3 hours. The fish were sacrificed, ashed overnight at 6008° C. and the isotope content of the ash was determined by scintillation counting. Based on body weight and the specific activity of the water, whole body $Ca^{++}$ uptake in each fish was expressed as µM Ca2+kg/hour. Both human and salmon STC had statistically significant inhibitory effects on gill Ca2+ transport at the doses employed (P<0.05, P,0.01) demonstrating that the bacterial expressed human stanniocalcin has biological activity in fish (FIG. 4).

EXAMPLE 5
Bacterial Expressed Human Corpuscles of Stannius Protein Reduces Renal Excretion of Phosphate Rats (250±10 g; 5 rats per group) were anesthetized with inactin and catheters were placed in the jugular vein and carotid arteries. The urethras were also catheterized for collection of urine. The animals were continuously infused with inulin and PAH, used for small unreactive compounds for the measurement of glomerular filtration and renal blood flow, respectively. The animals were also connected to a physiograph for monitoring of blood pressure and heart rate. Blood samples were taken from the carotid catheter. Animals were given a bolus injection of human Corpuscles of Stannius or saline via the jugular catheter after the first urine collection period (arrow) and monitored for changes in plasma and urinary electrolytes, renal function, heart rate and blood pressure.

Shown are the effects of a 5 n moles/kg body weight bolus injection of human stanniocalcin, delivered over 5 minutes (arrow). Controls received an equivalent volume of saline. Human stanniocalcin had no effect on heart rate or blood pressure (P<0.05, Students T-test). Excretion of electrolytes was measured as absolute excretion or as a proportion of renal filtered load reabsorbed by the kidneys (fractional excretion, FE). Only data for absolute excretion of phosphate was demonstrated to be significantly different from control animals. Plasma levels of calcium, phosphate, potassium and sodium did not significantly change. Absolute excretion of calcium and fractional excretion of calcium and phosphate did not change significantly. Absolute phosphate excretion was maximally suppressed 60 minutes after hormone delivery and remained significantly lower than the saline-injected controls until the end of the experiment (P<0.02) (FIG. 5).

EXAMPLE 6
Purification of Baculovirus-Expressed Human Corpuscles of Stannius Protein The human Stanniocalcin gene was cloned into the pRG1 baculovirus transfer vector. Culture supernatant from SF9 cells infected with recombinant baculovirus was collected, concentrated 10 times, and diafiltered to 50 mM Tris pH 7.0 and 500 mM NaCl. After centrifugation, the solution was applied to a conA column and washed using the same buffer followed by washing with 50 mM tris pH 7.0 and 50 mM NaCl. Following elution in 50 mM Tris, 100 mM Borate, 750 mM mannose and 750 mM dextrose, an equal volume of 50 mM MES pH 5.8 was added and the solution was applied to an ion exchange column (S column) and protein eluted by a gradient of NaCl.

Shown are four fractions eluted from the S column at 200–300 mM NaCl (FIG. 6). A) Analysis by SDS-PAGE, and B) Western blotting using a rabbit antibody raised against fish Stanniocalcin.

EXAMPLE 7
N-terminal Sequencing of Baculovirus Expressed Human Corpuscles of Stannius The material for sequencing Run #19 was obtained from baculovirus-expressed Corpuscles of Stannius by first applying the supernatant to a Con A column equilibrated with 50 mM Tris, pH 7.0, containing 0.5 M NaCl, 1 mM CaCl , 1 mM MgCl and 1 mM MgCl . The Corpuscles of Stannius was eluted with the above buffer containing 100 mM sodium $$\text{dextrose}^2$$

at pH 7.0, 0.75 M $$\text{borate}^2$$

and 0.75 M mannose. This fraction was then further purified using a reversed phase HPLC column (RP-300, 2.1×30 mm) equilibrated with 0.1% TFA (Solvent A). The proteins were eluted with a 7.5 min. gradient from 0% to 60% Solvent B (acetonitrile containing 0.07% TFA). A fraction which was positive by Western blot analysis was then sequenced (Run #19). The material for sequencing Run #26 was obtained from a supernatant containing baculovirus-expressed Corpuscles of Stannius which was concentrated 10-fold and diafiltered with 50 mM TrisHCl at pH 7.0 containing 500 mM NaCl. This concentrate was then applied to a Con A column equilibrated with this pH 7.0 Tris buffer, washed with 50 mM Tris-HCl at pH 7.0 containing 20 mM NaCl and then eluted using the same 50 mM Tris-HCl at pH 7.0 containing 20 mM NaCl with 100 mM sodium borate at pH 7.0, 0.75 M mannose and 0.75M dextrose. The fractions were pooled and an equal volume of 50 mM MES buffer at pH 5.8 was added. This solution was then applied to a SP-650M column (1.0×6.6 cm, Toyopearl) at a flow rate of 1 ml/min. Proteins were then eluted with step gradients at 200, 300 and 500 mM NaCl. The Corpuscles of Stannius was obtained using the elution at 300 mM NaCl. The partially purified material was spotted onto the ProBlott membrane (Applied Biosystems, Inc.) and subjected to amino acid sequence analysis. The underlined letters represent the N-terminal residues as determined by amino acid sequence analysis, and are reported as the N-terminal amino acid sequence of SEQ ID NO:2. The lower case letters are residues that could not be conclusively identified, but the results are consistent with the expected sequence. The colons indicate where the observed residues are identical to that expected from DNA sequencing.

monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HimdIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging

```
                (Run#26)
            THEAEONDSVSPrK (SEQ ID NO:2, amino acids -18 to -5)
            !!!!!!!!!!!!!!
MLQNSAVLLVLVISASATHEAEQNDSVSPRKSRVA
                !!!!!!!!!!!!!!
               AEONDSVSPRKsrva (SEQ ID NO:2, amino acids -15 to -1)
                  (Run #26)

(Run#19)
            AONSAEVVRcLNSAL (SEQ ID NO:2, amino acids 1 to 15)
            !!!!!!!!!!!!!!
            AQNSAEVVRCLNSALQVGCGAFACLE NSTCDTDGMYDICKSFLYSAAKFDTQGKAFVKESLKCIANGVTSKVRLAIRRCSTFQRMIAEVQEECYSKLN
VCSIAKRNPEAITEVVQLPNHFSNRYYNRLVRSLLECDEDTVSTIRDSLMEKIGPNMASLFHILQTDHCAQT
HPRADFNRRRTNEPQKLKVLLRNLRGEEDSPSHIKRTSHESA
```

As shown above, the N-terminal signal sequence begins with the initial methianine residue and ends between the two alanine residues at position 35 and 36. This has been deduced since a full-length protein is first processed between the alanine and threonine residues at positions 17 and 18 and is then further processed between the two alanine residues at positions 34 and 35 to produce the mature protein.

EXAMPLE 8

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 378° C. for approximately one week. At this time, fresh media is added and subsequently changed every several days. After an additional two weeks in culture, a cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

Numerous modifications and variations of the present invention are possible in light of the above teachings and, therefore, within the scope of the appended claims, the invention may be practiced otherwise than as particularly described.

What is claimed is:

1. An isolated polypeptide comprising a member selected from the group consisting of:
   (a) a polypeptide having an amino acid sequence according to amino acids 1 to 212 of SEQ ID NO:2;
   (b) a polypeptide which is a fragment of the amino acid sequence according to SEQ ID NO:2, wherein said fragment retains the calcium uptake inhibitory activity of the polypeptide according to SEQ ID NO:2; and
   (c) a polypeptide consisting of amino acid residues 1 to 20 of SEQ ID NO:2.

2. A polypeptide according to claim 1, comprising a member selected from (a), (b) or (c) and further comprising a pro-sequence that may be cleaved to provide a polypeptide comprising an active (a), (b) or (c) polypeptide.

3. An isolated polypeptide according to claim 1, comprising amino acids 1 to 212 of SEQ ID NO:2.

4. An isolated polypeptide according to claim 2, wherein said polypeptide comprises amino acids −35 to 212 of SEQ NO:2.

5. An isolated polypeptide according to claim 1, wherein said member is (b).

6. An isolated polypeptide comprising a member selected from the group consisting of:
   (a) a polypeptide encoded by the portion of the human cDNA of ATCC Deposit No. 75652 which encodes the mature polypeptide;
   (b) a polypeptide which is a fragment (a), wherein said fragment retains the calcium uptake inhibitory activity of the polypeptide of (a); and
   (c) a polypeptide consisting of the N-terminal 20 amino acids of the polypeptide encoded by the human cDNA of ATCC Deposit No. 75652.

7. A polypeptide according to claim 6, comprising a member selected from (a), (b) or (c) and further comprising a pro-sequence that may be cleaved to provide a polypeptide comprising an active (a), (b) or (c) polypeptide.

8. An isolated polypeptide according to claim 6 comprising the mature polypeptide of member (a).

9. An isolated polypeptide according to claim 7, wherein said polypeptide sequence comprises the polypeptide encoded by the human cDNA of ATCC Deposit No. 75652.

10. An isolated polypeptide according to claim 6, wherein said member is (b).

11. A method for the treatment of a patient having need to inhibit uptake of calcium comprising administering to the patient a therapeutically effective amount of the polypeptide of claim 1.

12. A method for the treatment of a patient having need to inhibit uptake of calcium comprising administering to the patient a therapeutically effective amount of the polypeptide of claim 3.

13. A method for the treatment of a patient having need to inhibit uptake of calcium comprising administering to the patient a therapeutically effective amount of the polypeptide of claim 5.

14. A method for the treatment of a patient having need to inhibit uptake of calcium comprising administering to the patient a therapeutically effective amount of the polypeptide of claim 6.

15. A method for the treatment of a patient having need to inhibit uptake of calcium comprising administering to the patient a therapeutically effective amount of the polypeptide of claim 8.

16. A method for the treatment of a patient having need to inhibit uptake of calcium comprising administering to the patient a therapeutically effective amount of the polypeptide of claim 10.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 771 BASE PAIRS
       (B) TYPE: NUCLEIC ACID
       (C) STRANDEDNESS: SINGLE
       (D) TOPOLOGY: LINEAR (ii) MOLECULE TYPE: cDNA (xi) SEQUENCE DESCRIPTION: SEQ ID NO:1:

```
GAAACTTCTC AGAGAATGCT CCAAAACTCA GCAGTGCTTC TGGTGCTGGT GATCAGTGCT    60
TCTGCAACCC ATGAGGCGGA GCAGAATGAC TCTGTGAGCC CCAGGAAATC CCGAGTGGCG   120
GCCCAAAACT CAGCTGAAGT GGTTCGTTGC CTCAACAGTG CTCTACAGGT CGGCTGCGGG   180
GCTTTTGCAT GCCTGGAAAA CTCCACCTGT GACACAGATG GGATGTATGA CATCTGTAAA   240
TCCTTCTTGT ACAGCGCTGC TAAATTTGAC ACTCAGGGAA AAGCATTCGT CAAAGAGAGC   300
TTAAAATGCA TCGCCAACGG GGTCACCTCC AAGGTCTTCC TCGCCATTCG GAGGTGCTCC   360
ACTTTCCAAA GGATGATTGC TGAGGTGCAG GAAGAGTGCT ACAGCAAGCT GAATGTGTGC   420
AGCATCGCCA AGCGGAACCC TGAAGCCATC ACTGAGGTCG TCCAGCTGCC CAATCACTTC   480
TCCAACAGAT ACTATAACAG ACTTGTCCGA AGCCTGCTGG AATGTGATGA AGACACAGTC   540
AGCACAATCA GAGACAGCCT GATGGAGAAA ATTGGGCCTA ACATGGCCAG CCTCTTCCAC   600
ATCCTGCAGA CAGACCACTG TGCCCAAACA CACCCACGAG CTGACTTCAA CAGGAGACGC   660
ACCAATGAGC CGCAGAAGCT GAAAGTCCTC CTCAGGAACC TCCGAGGTGA GGAGGACTCT   720
CCCTCCCACA TCAAACGCAC ATCCCATGAG AGTGCATAAC CAGGGAGAGG T            771
```

(2) INFORMATION FOR SEQ ID NO:2:

(i) SEQUENCE CHARACTERISTICS:
       (A) LENGTH: 247 AMINO ACIDS
       (B) TYPE: AMINO ACID
       (C) STRANDEDNESS:
       (D) TOPOLOGY: LINEAR (ii) MOLECULE TYPE: PROTEIN (xi) SEQUENCE DESCRIPTION: SEQ ID NO:2:

```
Met Leu Gln Asn Ser Ala Val Leu Leu Val Leu Val Ile Ser Ala
-35                 -30                 -25

Ser Ala Thr His Glu Ala Glu Gln Asn Asp Ser Val Ser Pro Arg
-20                 -15                 -10

Lys Ser Arg Val Ala Ala Gln Asn Ser Ala Glu Val Val Arg Cys
 -5                  1                   5                 10

Leu Asn Ser Ala Leu Gln Val Gly Cys Gly Ala Phe Ala Cys Leu
                    15                  20                 25

Glu Asn Ser Thr Cys Asp Thr Asp Gly Met Tyr Asp Ile Cys Lys
                    30                  35                 40

Ser Phe Leu Tyr Ser Ala Ala Lys Phe Asp Thr Gln Gly Lys Ala
                    45                  50                 55

Phe Val Lys Glu Ser Leu Lys Cys Ile Ala Asn Gly Val Thr Ser
                    60                  65                 70
```

```
Lys Val Phe Leu Ala Ile Arg Arg Cys Ser Thr Phe Gln Arg Met
             75                  80                  85

Ile Ala Glu Val Gln Glu Cys Tyr Ser Lys Leu Asn Val Cys
             90                  95                 100

Ser Ile Ala Lys Arg Asn Pro Glu Ala Ile Thr Glu Val Val Gln
            105                 110                 115

Leu Pro Asn His Phe Ser Asn Arg Tyr Tyr Asn Arg Leu Val Arg
            120                 125                 130

Ser Leu Leu Glu Cys Asp Glu Asp Thr Val Ser Thr Ile Arg Asp
            135                 140                 145

Ser Leu Met Glu Lys Ile Gly Pro Asn Met Ala Ser Leu Phe His
            150                 155                 160

Ile Leu Gln Thr Asp His Cys Ala Gln Thr His Pro Arg Ala Asp
            165                 170                 175

Phe Asn Arg Arg Arg Thr Asn Glu Pro Gln Lys Leu Lys Val Leu
            180                 185                 190

Leu Arg Asn Leu Arg Gly Glu Glu Asp Ser Pro Ser His Ile Lys
            195                 200                 205

Arg Thr Ser His Glu Ser Ala
            210
```

(2) INFORMATION FOR SEQ ID NO:3:

(i) SEQUENCE CHARACTERISTICS:
        (A) LENGTH: 27 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

GACTGCATGC TCCAAAACTC AGCAGTG                      27

(2) INFORMATION FOR SEQ ID NO:4:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

GACTAGATCT TGCACTCTCA TGGGATGTGC G                  31

(2) INFORMATION FOR SEQ ID NO:5:

(i) SEQUENCE CHARACTERISTICS:
        (A) LENGTH: 37 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:5:

CAGTGGATCC GCCACCATGC TCCAAAACTC AGCAGTG           37

(2) INFORMATION FOR SEQ ID NO:6:

(i) SEQUENCE CHARACTERISTICS:

```
        (A) LENGTH:  30 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:6:

CAGTGGTACC GGTTGTGAAT AACCTCTCCC                                        30

(2) INFORMATION FOR SEQ ID NO:7:

(i) SEQUENCE CHARACTERISTICS:
        (A) LENGTH:  37 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:7:

CAGTGGATCC GCCACCATGC TCCAAAACTC AGCAGTG                                37

(2) INFORMATION FOR SEQ ID NO:8:

(i) SEQUENCE CHARACTERISTICS:
        (A) LENGTH:  30 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:8:

CAGTGGATCC GGTTGTGAAT AACCTCTCCC                                        30
```